(12) United States Patent
Tournilhac et al.

(10) Patent No.: US 6,534,071 B1
(45) Date of Patent: Mar. 18, 2003

(54) COMPOSITION IN THE FORM OF AN OIL-IN-WATER EMULSION CONTAINING CELLULOSE FIBRILS, AND ITS USES, ESPECIALLY COSMETIC USES

(75) Inventors: Florence Tournilhac, Paris; Raluca Lorant, Thiais, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/573,175

(22) Filed: May 19, 2000

(30) Foreign Application Priority Data

Jun. 2, 1999 (FR) .............................. 99 06964

(51) Int. Cl.$^7$ .............................. A61K 7/00; A61K 7/48
(52) U.S. Cl. ..................... 424/401; 424/61; 424/70.1; 424/70.6; 424/78.03
(58) Field of Search ............................ 424/401, 47, 61, 424/70.1, 70.6, 78.03; 264/171; 554/79

(56) References Cited

U.S. PATENT DOCUMENTS

| | | | | |
|---|---|---|---|---|
| 4,710,336 A | * | 12/1987 | Credall et al. | 264/171 |
| 5,632,998 A | * | 5/1997 | Midha et al. | 424/401 |
| 5,833,951 A | * | 11/1998 | Artz et al. | 424/47 |
| 6,133,463 A | * | 8/1999 | Fourneron et al. | 554/79 |
| 6,001,338 A | * | 12/1999 | Mondet | 424/61 |

FOREIGN PATENT DOCUMENTS

FR 2 744 632 8/1997

OTHER PUBLICATIONS

Database Promt 'Online!, News Release, Apr. 23, 1990 (1pp.); "Weyerhaeuser intros cellulose product 300 times finer than wood pulp; coating, biding, thickening uses as see" XP002130638.

Database WPI, Section Ch, Week 198713; Derwent Publications Ltd., London, GB; Class A96, AN 1987–089848, XP002130639 & JP 62 039507, Feb. 20, 1987.

Hiroshi Ougiya, et al.; "Emulsion–stabilizing Effect of Bacterial Cellulose"; Biosci., Biotechnol., Biochem., vol. 61, No. 9, pp. 1541–1545; 1997; XP000876735.

* cited by examiner

Primary Examiner—Jose' G. Dees
Assistant Examiner—M. Haghighatian
(74) Attorney, Agent, or Firm—Oblon, Spivak, McClelland, Maier & Neustadt, P.C.

(57) ABSTRACT

The present application relates to a composition in the form of an oil-in-water emulsion comprising an oily phase dispersed in an aqueous phase, characterized in that the composition is free of surfactant and in that it contains cellulose fibrils which have a length of greater than 1 micron and a length/diameter ratio of greater than 30. The invention also relates to the use of the composition, especially for the care, the treatment, the makeup or the cleansing of the skin, lips, eyelashes and/or hair, as well as for the care of sensitive or dry skin.

14 Claims, No Drawings

COMPOSITION IN THE FORM OF AN OIL-IN-WATER EMULSION CONTAINING CELLULOSE FIBRILS, AND ITS USES, ESPECIALLY COSMETIC USES

BACKGROUND OF THE INVENTION

1. Field of the Invention

The present application relates to a composition in the form of an oil-in-water emulsion preferably free of surfactant, and containing cellulose fibrils, and to the use of the composition, particularly for the care, the treatment and/or the makeup of the body's skin, face, hair, eyelashes and/or lips. The application also relates to the use of cellulose fibrils for stabilizing an oil-in-water emulsion that is free of surfactant.

2. Discussion of the Background

For various reasons particularly associated with greater comfort in use (softness, emollience and the like), current cosmetic compositions are usually in the form of an emulsion of the oil-in-water (O/W) type consisting of an aqueous dispersing continuous phase and an oily dispersed discontinuous phase or of an emulsion of the water-in-oil (W/O) type consisting of an oily dispersing continuous phase and an aqueous dispersed discontinuous phase. O/W emulsions are the most demanded in the cosmetic field because they have, as external phase, an aqueous phase, giving them a cooler, less greasy and lighter feel during application to the skin than W/O emulsions.

Emulsions are generally stabilized by suitable emulsifying surfactants which, because of their amphiphilic structure, lie at the oil/water interface and thus stabilize the dispersed droplets. However, these emulsifiers have the drawback of being penetrants and potentially irritants for the skin, eyes and scalp, especially for users with sensitive skin.

Furthermore, such emulsions may have insufficient cosmetic and physicochemical properties (oily feel, instability over time). Increasing the amount of surfactants does not generally solve the problems mentioned. The required stability is not always achieved and the cosmetic properties are not improved (waxy, heavy feel, lack of coolness at application). Moreover, as indicated above, it is also not recommended to use too high a surfactant content for reasons of innocuousness.

One solution for overcoming instability phenomena (creaming and phase separation) in O/W emulsions consists in adding thickeners to the emulsion, the function of these thickeners being to create, within the aqueous phase, a gelled matrix serving to fix the oily droplets and ensuring mechanical integrity of the entire emulsion. However, this solution has the drawback of not making it possible to obtain all the desired textures, and in particular the light textures, which are easily and quickly applied to the skin without leaving a residual film.

Moreover, it has been envisaged to replace the surfactants with polymers having, in their chain, a hydrophilic part and a hydrophobic part consisting of a fatty chain, such as $C_{10}$–$C_{30}$ alkyl acrylate/acrylic or methacrylic acid copolymers, such as the product "PEMULEN TR2" sold by Goodrich. However, these polymers have the drawback of providing a tacky effect on applying them to the skin and of not allowing a composition to be obtained which remains stable over a long period of time when the amount of oil is too great.

OBJECTS OF THE INVENTIONS

One objective of the invention is to be able to produce stable oil-in-water emulsions not containing an emulsifying surfactant conventionally used in O/E emulsions, and having good cosmetic properties without having the drawbacks of the prior art. Another object is stable O/E emulsions in general.

SUMMARY OF THE INVENTION

The inventors have discovered unexpectedly that cellulose fibrils can be used to produce stable oil-in-water emulsions, although free of surfactant.

DETAILED DESCRIPTION OF THE INVENTION

While it is known practice to use cellulose fibrils in cosmetic compositions, it has never been envisaged to use them in O/W emulsions to stabilize these emulsions in the absence of any surfactant.

The present invention relates to a composition in the form of an oil-in-water emulsion comprising, in a physiologically acceptable medium, an oily phase dispersed in an aqueous phase, characterized in that the composition is free of surfactant and in that it contains cellulose fibrils which preferably have a length of greater than 1 micron and a length/diameter ratio of greater than 30.

Another subject of the invention is the use of cellulose fibrils for stabilizing an oil-in-water emulsion free of surfactant, and emulsions so stabilized.

The composition obtained has a homogeneous and pleasant texture at application. Furthermore, although free of surfactant, it remains stable over time at room temperature or at higher temperatures. In addition, because of the absence of surfactant, it has the advantage of not being an irritant for the skin, particularly sensitive skin, and of furthermore allowing the incorporation of heat-sensitive active agents, since it can be manufactured at room temperature.

The expression "physiologically acceptable medium" should be understood to mean here a medium compatible with the skin, lips, scalp, eyelashes, eyes and/or hair.

Moreover, the term "cellulose fibrils" should be understood in the present application to include both nanofibrils and microfibrils. These fibrils have a length of greater than 1 $\mu$m and preferably ranging from 5 to 40 $\mu$m, including 10, 15, 20, 25, 30 and 35 $\mu$m, and a length/diameter ratio equal to or greater than 30, including 35, 40, 45, 50, etc. The diameter of the fibrils used may range, for example, from 2 to 100 nm (0.002 to 0.1 $\mu$m) including 5, 10, 20, 30, 40, 50, 60, 70, 80 and 90 nm.

The cellulose fibrils used according to the invention are preferably amorphous, that is to say they preferably have a degree of crystallinity of less than or equal to 50% and preferably ranging from 15 to 50% including 20, 25, 30, 35, 40 and 45%.

Furthermore, the cellulose fibrils used according to the invention may be obtained in any manner including either by mechanical or chemical extraction from plants or algae, or by bacterial fermentation. Moreover, they may be in the form of dry matter or in a dispersion, especially an aqueous dispersion.

The cellulose fibrils used according to the invention may be as produced or they may be modified. Thus, they may be mixed with an additive, and especially with carboxylated cellulose, as described in the documents WO-A-98/02486 and WO-A-98/02487. They may also be in modified form, for example they may be modified by carboxylic acids as described, for example, in document EP-A-726,356, and/or combined with a polyhydroxylated organic compound, as described for example in document FR-A-2,769,836.

The cellulose fibrils used according to the invention are preferably those obtaining after mixing, in an aqueous medium, of cellulose fibrils and carboxylated cellulose, especially carboxymethylcellulose, and drying of this mixture, such as described in the document FR-A-2,769,836.

In particular, it is possible to use, as cellulose fibrils, those sold under the names "CELLULON" by Kelco, that sold under the name "FIBRILIANCE" by Soliance and those from Rhodia, especially that called hereafter "Compound A", which comprises 85% of nanofibrils and 15% of carboxymethylcellulose and are obtained according to Example 1 of the document FR-A-2,769,836.

The cellulose fibrils are generally introduced into the aqueous phase of the emulsion.

The composition of the invention may preferably contain an amount of cellulose fibrils ranging from 0.05 to 20% by weight, including 1, 3, 5, 8, 10, 12, 15, 17 and 19% preferably from 0.1 to 10% and even better from 0.5 to 5% by weight, with respect to the total weight of the composition.

The oily phase of the composition according to the invention generally represents from 10 to 40% and preferably from 15 to 30% by weight with respect to the total weight of the composition.

The oily phase may contain any of the fatty substances, and especially oils, conventionally used in the cosmetic or dermatological fields.

Among the oils that can be used in the emulsion of the invention, mention may be made, for example, of plant oils such as jojoba, avocado, soft-almond, apricot and corn oils and the liquid fraction of karite butter; mineral oils such as liquid paraffin and hydrogenated polyisobutylene; synthetic oils such as 2-ethylhexyl palmitate, isopropyl myristate, hydrogenated isoparaffin, isononyl isononanoate and cetearyl octanoate; volatile or non-volatile silicone oils and fluorinated oils. The other fatty substances that can be present in the oily phase may, for example, be fatty acids, fatty alcohols and waxes.

According to one particular embodiment of the invention, the composition of the invention contains at least one mineral oil such as liquid paraffin and hydrogenated polyisobutylene. According to a more particularly preferred embodiment, the mineral oil is liquid petroleum which makes it possible to obtain compositions having a particularly pleasant texture.

Thus, according to one particular embodiment of the invention, the composition according to the invention comprises at least 5% by weight, preferably at least 10% by weight and even more preferably 15% by weight of the mineral-oil, and especially of liquid paraffin, with respect to the total weight composition.

The aqueous phase of the composition of the invention generally constitutes from 60 to 90% and preferably from 70 to 85% by weight with respect to the total weight of the composition.

In a known manner, the compositions of the invention may contain standard additives in the fields in question, such as hydrophilic or lipophilic active agents, preservatives, gelling agents, antioxidants, fragrances, solvents, fillers and especially fillers producing a matting effect or nacres, filters, colorants (pigments or soluble dyes), base or acid agents, and also lipid vesicles. These additives are used in the usual proportions in the cosmetic field, and for example from 0.01 to 30% of the total weight of the emulsion, and they are, depending on their nature, introduced into the aqueous phase or into the oily phase of the emulsion, or even in vesicles. These additives and their concentrations must be such that they do not modify the property desired for the emulsion of the invention.

As active agents, mention may be made, for example, of hydrating agents, such as polyols like glycerol and sorbitol; keratolytic agents; depigmenting agents; thinners, and any active agent suitable for the final purpose of the composition.

Depending on the fluidity of the composition that it is desired to obtain, it is possible to add to it one or more hydrophilic or lipophilic gelling agents. As hydrophilic gelling agents, mention may be made, for example, of cellulose derivatives such as carboxymethylcellulose; polysaccharide gums and their derivatives (xanthan gum, carboxymethyl-hydroxypropyl guar); proteins; acrylic and vinyl polymers; associative polymers, such as polyurethanes, polyacrylics or polyacrylamides, and modified natural polymers. As lipophilic gelling agents, mention may be made of acrylic copolymers such as the one sold under the name "STRUCTURE O" by National Starch (CTFA name: acrylates copolymer); hydrophobic modified-guar derivatives; polyethylene derivatives; styrene-ethylene-butylene-styrene, styrene-butylene-styrene and styrene-ethylene-styrene triblock elastomers; clays, such as bentone. It is also possible to use a mixture of these gelling agents.

These gelling agents, when they are present, are generally used in concentrations ranging from 0.1 to 10%, preferably from 0.1 to 5% and even better from 0.1 to 3%, by weight of active material with respect to the total weight of the composition.

The compositions forming the subject of the invention find their application in a large number of treatments, especially cosmetic treatments and can thus form a cosmetic composition, especially for the treatment, the protection, the care, the makeup-removal from and/or the cleansing of the skin, lips and/or hair, and/or as makeup for the skin, lips, eyelashes and/or body.

The compositions according to the invention may, for example, be used as beauty care, makeup-removal and/or cleansing products for the face in the form of creams or milks or as makeup products (skin, eyelashes and lips) by the incorporation of pigments or dyes, for example as foundations or as mascaras.

In addition, the subject of the invention is the cosmetic use of the composition as defined above for the treatment, the protection, the care and the makeup-removal from and/or the cleansing of the skin, lips and/or hair, and/or as makeup for the skin, lips, eyelashes and/or body.

The subject of the invention is also a process for the cosmetic treatment of the skin, including the scalp, hair, eyelashes and/or lips, characterized in that a composition as defined above is applied to the skin, to the hair, to the eyelashes and/or to the lips.

Because of the fact that the composition is free of surfactant, it is particularly well tolerated by users having sensitive skin. Moreover, it is also suitable for dry skin.

The subject of the invention is also the use of the composition as defined above for the manufacture of a composition intended for the care of dry and/or sensitive skin.

The examples which follow will allow the invention to be more clearly understood without, however, implying any limitation. Unless otherwise mentioned, the amounts indicated are in % by weight.

EXAMPLES

Example 1

Cream

| Aqueous phase: | |
| --- | --- |
| Cellulose nanofibrils | 1% |
| (Compound A from Rhodia) | |
| Preservatives | 0.3% |
| Demineralized water | qsp 100% |
| Oily phase: | |
| Liquid paraffin | 20% |

Operating Method: The aqueous phase is homogenized by dispersing it using the homogenizer under pressure. The oily phase is then added thereto and the mixture undergoes a further two pressurized homogenization passes.

A cream is obtained which, when applied to the skin, is cool like a milk, while being nutritive. This cream is particularly suitable for the care of dry skin and sensitive skin.

Example 2

Nutritive Cream for Sensitive Skin

| Aqueous phase: | |
| --- | --- |
| Preservatives | 0.3% |
| Glycerol | 5% |
| Cellulose microfibrils | 1.7% |
| (Cellulon PC from Kelco) | |
| Carboxymethylcellulose | 0.3% |
| Demineralized water | qsp 100% |
| Oily phase: | |
| Apricot kernel oil | 10% |
| Hydrogenated polyisobutylene | 5% |
| Acrylates copolymer | 1% |
| (Structure O from National Starch) | |

Operating Method: The aqueous phase is homogenized by simple stirring, then the oily phase, prehomogenized at 70° C., is dispersed therein with stirring.

A cream particularly well tolerated by users with sensitive skin is obtained.

Example 3

Foundation

| Aqueous phase: | |
| --- | --- |
| Cellulose microfibrils | 1% |
| (Compound A from Rhodia) | |
| Preservatives | 0.3% |
| Demineralized water | qsp 100% |
| Oily phase: | |
| Liquid paraffin | 20% |
| Iron oxides | 4% |
| Titanium oxide | 1% |

Operating Method: The aqueous phase is prepared in an homogenizer with stirring, and then the oily phase, prepared beforehand by grinding the pigments in oil, is added thereto.

A foundation having the appearance of a cream is obtained, this being easy to spread and to make uniform, like a liquid foundation.

All documents referred to above are incorporated herein by reference. Also, French patent application 99 06964 is incorporated herein by reference.

What is claimed is:

1. A composition in the form of an oil-in-water emulsion comprising an oily phase dispersed in an aqueous phase, wherein said composition is free of surfactant and comprises cellulose fibrils which have a length of greater than 1 micron and a length/diameter ratio of greater than 30 and wherein the oily phase represents from 10 to 40% by weight of the composition based on the total weight of the composition.

2. A composition according to claim 1, wherein the cellulose fibrils have a length ranging from 5 to 40 μm.

3. A composition according to claim 1, wherein the cellulose fibrils have a diameter ranging from 2 to 100 nm.

4. A composition according to claim 1, wherein the cellulose fibrils are mixed with carboxylated cellulose, are modified by carboxylic acids, are combined with a polyhydroxylated organic compound or a combination thereof.

5. A composition according to claim 1, wherein the cellulose fibrils are obtained after mixing, in an aqueous medium, cellulose fibrils and carboxylated cellulose, and drying of this mixture.

6. A composition according to claim 1, wherein the cellulose fibrils are present in an amount ranging from 0.05 to 20% by weight with respect to the total weight of the composition.

7. A composition according to claim 1, wherein the oily phase comprises at least one mineral oil.

8. A composition according to claim 7, wherein the oily phase comprises liquid paraffin, hydrogenated polyisobutylene or a combination thereof.

9. A composition according to claim 7, wherein the oily phase comprises at least 5% by weight of mineral oil, with respect to the total weight composition.

10. A composition according to claim 1, further comprising at least one hydrophilic or lipophilic gelling agent.

11. A composition according to claim 1, wherein said composition is a cosmetic composition.

12. A method for the treatment, the protection, the care, the make-up-removal from or the cleansing or make-up of the skin, lips, hair or a combination thereof, comprising:
applying the composition of claim 1 to the skin, lips, eyelashes, body or a combination thereof.

13. The method of claim 12, wherein said composition is applied to dry skin, sensitive skin or a combination thereof.

14. A method for stabilizing an oil-in-water emulsion which is free of surfactant, comprising:
mixing components of said oil-in-water emulsion with cellulose fibrils having a length of greater tan 1 micron and a length/diameter ratio of greater than 30, mixing said fibrils into said emulsion, or a combination thereof, wherein the oily phase of the emulsion represents from 10 to 40% by weight of the product emulsion based on the total weight of the emulsion.

* * * * *

UNITED STATES PATENT AND TRADEMARK OFFICE
CERTIFICATE OF CORRECTION

PATENT NO.    : 6,534,071 B1                                              Page 1 of 1
DATED         : March 18, 2003
INVENTOR(S)   : Florence Tournilhac et al.

It is certified that error appears in the above-identified patent and that said Letters Patent is hereby corrected as shown below:

Column 6,
Line 60, "tan" should read -- than --.

Signed and Sealed this

First Day of July, 2003

JAMES E. ROGAN
*Director of the United States Patent and Trademark Office*